United States Patent [19]

Winters et al.

[11] 3,984,563

[45] Oct. 5, 1976

[54] ANTIINFLAMMATORY 2-IMINO-INDOLINES AND THEIR PHARMACEUTICAL COMPOSITIONS

[75] Inventors: Giorgio Winters; Nunzio Di Mola, both of Milan, Italy

[73] Assignee: Gruppo Lepetit S.p.A., Milan, Italy

[22] Filed: Sept. 9, 1974

[21] Appl. No.: 504,205

[30] Foreign Application Priority Data

Sept. 10, 1973 United Kingdom............... 42367/73

[52] U.S. Cl. .................... 424/274; 260/247.2 A; 260/247.5 FP; 260/326 N; 260/326.11 R; 260/326.14 R; 260/326.14 A; 260/326.15; 260/488 CD; 260/518 R; 260/562 H; 424/248; 424/309; 424/317; 424/324
[51] Int. Cl.² .............. C07D 209/14; A61K 31/40
[58] Field of Search ............. 260/326.11 R, 326.15, 260/326.14 A; 424/274

[56] References Cited
UNITED STATES PATENTS 3,320,278  5/1967  Ruyle et al. ................. 260/326.14 A
3,869,471  3/1975  Richter et al. ............... 260/326.11 R

FOREIGN PATENTS OR APPLICATIONS 913,931  12/1962  United Kingdom ........ 260/326.11 R

OTHER PUBLICATIONS

Kebrle et al., Chem. Abstracts, vol. 50, pp. 6426i–64-27i (1956).
Kost et al., Chem. Abstracts, vol. 76, pp. 301–302, No. 34047e and Chem. Subst. Index, 2H–Indol–2–imine (1972).
Golubeva et al., Chem. Abstracts, vol. 79, p. 433, No. 31782s and Chem. Subst. Index, 2H–Indol–2–imine (1973).

Primary Examiner—Lewis Gotts
Assistant Examiner—S. P. Williams
Attorney, Agent, or Firm—Theodore Post; C. Kenneth Bjork

[57] ABSTRACT

Compounds with antiinflammatory, analgesic and CNS depressant activity having the following general formula

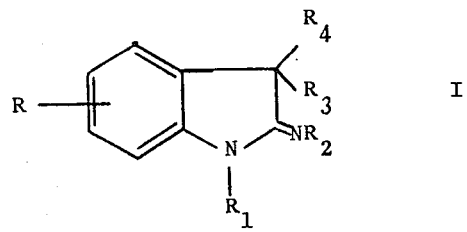

I wherein

R represents hydrogen or methoxy;

$R_1$ represents hydrogen; lower alkyl; lower alkyl substituted with a group carboxy, carbo(lower alkoxy) or carbamyl; phenyl; benzyl, lower aliphatic acyl; benzoyl; benzoyl substituted with a halo group;

$R_2$ represents hydrogen; lower alkyl; carbo(lower alkoxy); carbamyl; phenylcarbamyl; lower aliphatic acyl; benzoyl; benzoyl substituted with a halo group, $R_3$ represents halo; lower alkyl; lower alkyl substituted with a group selected from carboxy, carbo(lower alkoxy), carbamyl, halo, amino, mono and di-lower alkylamino, phthalimido and morpholino; phenyl; phenyl substituted with a group selected from lower alkoxy, halo, nitro, amino and acetamido;

$R_4$ represents hydrogen or lower alkyl; with the proviso that when simultaneously $R_1$ represents hydrogen, methyl, phenyl, benzyl, acetyl or benzoyl, $R_2$ represents hydrogen, lower alkyl or acetyl, $R_3$ represents lower alkyl or phenyl, $R_4$ must be different from hydrogen and methyl;

or $R_3$ and $R_4$ taken together with the adjacent carbon atom may represent a 5–6 membered alicyclic ring.

2 Claims, No Drawings

ANTIINFLAMMATORY 2-IMINO-INDOLINES AND THEIR PHARMACEUTICAL COMPOSITIONS

SUMMARY OF THE INVENTION

The present invention relates to new pharmacologically active indole derivatives. The new compounds have the following general formula:

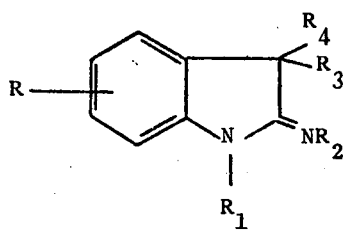

I wherein
R represents hydrogen or methoxy;

$R_1$ represents hydrogen; lower alkyl; lower alkyl substituted with carboxy, carbo(lower alkoxy) or carbamyl; phenyl; benzyl; lower aliphatic acyl; benzoyl; benzoyl substituted with a halo group;

$R_2$ represents hydrogen; lower alkyl; carbo(lower alkoxy); carbamyl; phenylcarbamyl; lower aliphatic acyl; benzoyl; benzoyl substituted with a halo group;

$R_3$ represents halo; lower alkyl; lower alkyl substituted with a group selected from carboxy, carbo(lower alkoxy), carbamyl, halo, amino, mono and di-lower alkylamino, phthalimido and morpholino; phenyl; phenyl substituted with a group selected from lower alkoxy, halo, nitro, amino and acetamido;

$R_4$ represents hydrogen or lower alkyl; with the proviso that when simultaneously $R_1$ represents hydrogen, methyl, phenyl, benzyl, acetyl or benzoyl, $R_2$ represents hydrogen, lower alkyl or acetyl; $R_3$ represents lower alkyl or phenyl, $R_4$ must be different from hydrogen and methyl;

or $R_3$ and $R_4$ taken together with the adjacent carbon atom may represent a 5–6 membered alicyclic ring.

In the specification and in the claims the term "lower alkyl" and the alkyl portion in the term "lower alkoxy" refers to an alkyl radical containing 1 to 4 carbon atoms such as methyl, ethyl, propyl, isopropyl, butyl, isobutyl and tert-butyl; the term "halo" identifies chloro, fluoro and bromo; the term "lower aliphatic acyl" refers to an alkanoyl radical of 1 to 4 carbon atoms, e.g. formyl, acetyl, propionyl, butyryl and isobutyryl.

It is obvious that when $R_1$ and/or $R_4$ represent hydrogen the following tautomeric forms of the inventive compounds of formula I are possible where the hydrogen atom has migrated on the iminic nitrogen:

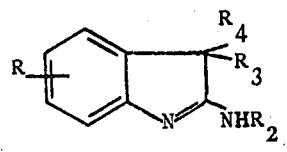

Ia
3H-indole

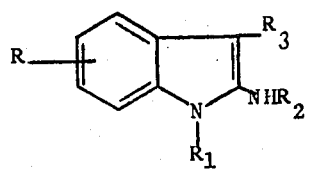

Ib
1H-indole

Also these tautomers fall within the scope of the invention as well as the addition salts of the compounds of formula I, Ia and Ib with pharmaceutically acceptable acids.

The compounds of the invention have a remarkable antiinflammatory and CNS depressant activity and moreover some members of this class are useful intermediates for the synthesis of new pharmacologically active heterocyclic derivatives such as for instance 3,4-dihydro-pyrido[2,3-b]indole-2(3H)-ones.

A preferred group of compounds comprises those derivatives of the formula I wherein R is hydrogen, $R_1$ represents hydrogen, lower alkyl or phenyl; $R_2$ represents hydrogen, lower alkyl, lower aliphatic acyl or benzoyl; $R_3$ and $R_4$ taken together with the adjacent carbon atom represent a cyclohexane ring. Within this group of compounds the most preferred ones are those wherein $R_1$ is methyl and $R_2$ is hydrogen. Representative compounds of this group besides the antiinflammatory properties possess also a remarkable analgesic activity.

A further object of the invention is to provide pharmaceutical compositions containing as the active ingredient a compound of the formula I wherein R, $R_1$, $R_2$, $R_3$ and $R_4$ have the same meaning as before.

Another feature of the invention consists in that some starting compounds for preparing the indole of the formula I, Ia and Ib display remarkable antiinflammatory properties. Accordingly, a further object of this invention is to provide pharmaceutical compositions comprising as the active ingredient a compound of the formula II

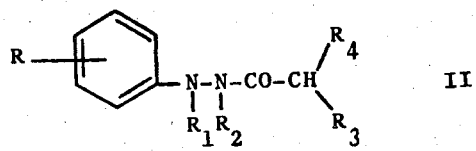

II wherein R is hydrogen or methoxy; $R_1$ is lower alkyl; $R_2$ is hydrogen or lower alkyl; $R_3$ is halo, lower alkyl, lower alkyl substituted with a group selected from carboxy, carbo(lower alkoxy), carbamyl, halo, amino, mono and di-lower alkylamino, phthalimido and morpholino; phenyl substituted with a group selected from lower alkoxy, halo, nitro, amino and acetamido; $R_4$ is hydrogen or lower alkyl or $R_3$ and $R_4$ taken together with the adjacent carbon atom may represent a 5–6 membered alicyclic ring.

DESCRIPTION OF THE PREFERRED EMBODIMENTS

The process for preparing the compounds of formula I is substantially analogous to that described by A. N. Kost et al. in Dokl. Akad. Nauk. SSSR, 200 (2), 342, 1971 (C.A. 76, 34047e) for preparing some members of the class where one of the substituents $R_3$ and $R_4$ is hydrogen and the other is phenyl or lower alkyl.

This process substantially consists in a Fischer-like cyclization of 1-phenyl-2-acyl-hydrazines II according to the following scheme:

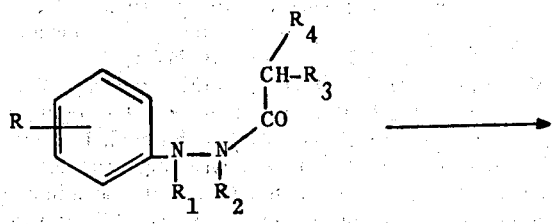

wherein

R represents hydrogen or methoxy;

$R_1$ represents hydrogen; lower alkyl; lower alkyl substituted with carbo(lower alkoxy); phenyl; and benzyl; and $R_2$ represents hydrogen or lower alkyl;

$R_3$ represents halo; lower alkyl; lower alkyl substituted with a group selected from carbo(lower alkoxy), halo, amino, mono and di-lower alkylamino, phthalimido and morpholino; phenyl; phenyl substituted with a group selected from lower alkoxy, halo, and nitro;

$R_4$ represents hydrogen or lower alkyl with the proviso that when simultaneously: $R_1$ represents methyl, phenyl or benzyl, $R_2$ represents lower alkyl, $R_3$ represents lower alkyl or phenyl, $R_4$ is different from hydrogen or methyl;

or $R_3$ and $R_4$ taken together with the adjacent carbon atom may represent a 5–6 membered alicyclic ring.

It is obvious from the above reaction scheme that most of the compounds falling within the general formula I are obtainable directly from the cyclization of a suitable acylhydrazine derivative. In turn, when according to the same reaction scheme an indole derivative is obtained wherein $R_1$ and/or $R_2$ are hydrogen, this may be further converted through common procedures to a compound falling within the scope of formula I as defined before. In actual practice, the cyclization process is carried out by adding to the predetermined hydrazine II a condensing agent and then maintaining the mixture at a temperature varying from about 10° C to about 150° C for a time varying from a few minutes to 5–7 hours. The reaction is preferably carried out in the presence of an organic inert solvent such as carbon tetrachloride, dioxane, benzene, chloroform, toluene, xylene and the like or an excess of the same condensing agent may be used instead of the organic solvent. The condensing agent may be employed in an amount which varies from about one molecular proportion to a large excess in respect to the hydrazine. Compounds like $POCl_3$, $PCl_5$, $PBr_3$, $PCl_3$, triphenylphosphine-carbon tetrachloride mixtures and phosgene are advantageously employed as the condensing agent. The crude end compound of formula I wherein $R_1$ is hydrogen, lower alkyl, substituted lower-alkyl, phenyl or benzyl and $R_2$ is hydrogen or lower alkyl are generally recovered directly from the reaction mixture as the hydrohalide by filtration or by distilling off the solvent and by adding to the residue a lower alkanol or a mixture of ethyl ether with a lower alkanol. Crystallization from common solvents affords the pure compounds.

The derivatives of formula I wherein $R_1$ is lower aliphatic acyl, benzoyl or substituted benzoyl and/or $R_2$ is carbo(lower alkoxy), lower aliphatic acyl, benzoyl, substituted benzoyl, carbamyl or phenylcarbamyl are prepared from the corresponding analogs wherein $R_1$ and/or $R_2$ is hydrogen through simple acylation or carbamylation procedures such as reaction with acids chlorides or anhydrides or with isocyanic acid or phenyl isocyanate.

The compounds wherein the radicals $R_1$ or $R_3$ contain a substituent such as carboxy or carbamyl may be prepared also from the corresponding carbalkoxy derivatives respectively by alkaline hyrolysis or by reaction with ammonium hydroxide in lower alkanols.

The compounds wherein $R_3$ is phenyl substituted with amino or acetamido are prepared respectively by catalytic hydrogenation of the nitro analogs and by acetylation with acetyl chloride or anhydride of the amino compounds obtained accordingly.

The starting 1-phenyl-2-acyl hydrazines II are new or literature compounds which may be prepared by acylation of the corresponding hydrazines.

The anti-inflamatory activity of the indole derivatives is evidenced by means of the carrageenin edema test in rats. In representative experiments compounds of formula I provoked a substantial decrease of the induced edema at dosage levels from about one fifth to about one tenth of their respective $LD_{50}$ values. The following table reports the results of the experiments:

| Compound of the example No. | Dose mg/kg.p.o. in rats | % Decrease of the edema | $LD_{50}$ mg/kg. p.o. in rats |
|---|---|---|---|
| 9 | 100 | 30 | >1000 |
|  | 200 | 41 |  |
| 13 | 8 | 45 | 100 |
|  | 20 | 60 |  |
| 28 | 100 | 35 | >1000 |
|  | 200 | 45 |  |
| 34 | 200 | 33 | >1000 |

Moreover, the compound of Example 13, tested for the analgesic effect on pain threshold of inflammed foot of the rat (L.O. Randall and J.J. Selitto: Arch. int. pharmacodyn, 1957, No. 4, 409–419) proved to be about 25 times as active as acetylsalicylic acid.

The following table reports the percent inhibitory effect of some representative compounds of the formula II in the carrageenin edema test.

| Compound | Dose mg/kg. p.o. in rats | % Decrease of the edema | LD₅₀ mg/kg. p.o. in rats |
|---|---|---|---|
| 1-Phenyl-1-methyl-2-cyclohexanoyl hydrazine | 50 | 37 | 500 |
| 1-Phenyl-1-methyl-2-acetylhydrazine | 50 | 57 | 500 |
| 1-Phenyl-1-methyl-2-isobutyrylhydrazine | 50 | 36 | 500 |
| 1-Phenyl-1-methyl-2-propionylhydrazine | 50 | 30 | 500 |
| 1-Phenyl-1-methyl-1-(phthalimido-butyryl)-hydrazine | 200 | 28 | >1000 |
| 1-Phenyl-1-methyl-2-cyclopentanoylhydrazine | 50 | 37 | 500 |
| 1-Phenyl-1-methyl-2-cyclopropanoylhydrazine | 50 | 35 | 500 |
| 1-Phenyl-1-methyl-2-(2-methylbutyryl)-hydrazine | 100 | 40 | >1000 |
| 1-(p-Methoxyphenyl)-1-methyl-2-isobutyrylhydrazine | 50 | 30 | 500 |

The compounds the invention may be administered by various routes such as, for instance, orally, rectally, or intramuscularly. The oral route is the most preferred one. For oral administration the substances are compounded in such forms as tablets, dispersible powders, capsules, granules, syrups, elixirs and solutions.

The compositions for oral use may contain one or more conventional adjuvants, such as, for instance, sweetening agents, flavoring agents, coloring agents, coating and preservative agents, in order to provide an elegant and palatable preparation. Tablets may contain the active ingredient admixed with conventional pharmaceutically acceptable excipient, e.g. inert diluents, such as calcium carbonate, sodium carbonate, lactose and talc, granulating and disintegrating aents, such as, for instance, starch, alginic acid and sodium carboxymethylcellulose, binding agents, e.g., starch, gelatin, gum-arabic and polivinylpyrrolidone and lubricating agents, e.g., magnesium stearate, stearic acid and talc. The tablets may be uncoated or coated by known techniques to delay disintegration and absorption in the gastrointestinal tract in order to provide long acting compositions. Syrups, elixirs and solutions are formulated as known in the art. Together with the active compound they may contain suspending agents, as, for instance methylcellulose, hydroxyethylcellulose, tragacanth and sodium alginate, wetting agents, e.g. lecithin, polyoxyethylene stearates and polyoxyethylene sorbitan monooleate, and the common preservative, sweetening and buffering agents.

A capsule or a tablet may contain the active ingredient alone or admixed with an inert solid diluent, such as, for instance, calcium carbonate, calcium phosphate and kaolin.

For rectal administration the compounds are administered in the form of suppositories, admixed with conventional vehicles, such as, for example, cocoa butter, wax, spermaceti or polyoxyethyleneglycols and their derivatives.

Although the oral and the rectal route are the preferred ways of administering the compounds of the invention, other useful routes may be suitably employed, such as, for instance, the intramuscular administration.

The active ingredient is thus embodied into injectable dosage forms. Such compositions are formulated as known in the art and may contain appropriate dispersing or wetting agents and suspending or buffering agents identical or similar to those mentioned above.

The compounds of the formula I and II above may be administered also in the form of their non-toxic pharmaceutically acceptable acid addition salts.

Such salts possess the same degree of activity as the free bases, from which they may be readily prepared by reaction with an appropriate acid and accordingly, are included within the scope of the invention. Representative of such salts are the mineral acid salts, such as, for instance, the hydrochloride, hydrobromide, sulfate, phosphate and the like and the organic acid salts such as the succinate, benzoate, acetate, p-toluenesulfonate, benzene sulfonate, maleate, tartrate, methanesulfonate, cyclohexylsulfonate and the like.

The dosage of active ingredient employed for combatting inflammatory or painful states in mammals, may vary depending on the compound employed and the severity of the condition being treated. Generally, good results are obtained when compounds of the above formula I and II are administered at a daily dosage of from about 0.5 to about 50 mg/kg. of animal body weight, preferably given in divided dose from two to six time a day.

The dosage forms useful for this purpose generally contain from about 5 to about 600 mg. of the active ingredient in admixture with a solid or liquid pharmaceutically acceptable carrier or diluent.

The following examples are given to illustrate the invention without limiting the scope thereof.

EXAMPLE 1

1-Methyl-3-morpholinoethyl-2-iminoindoline dihydrochloride

Twelve grams of 1-phenyl-1-methyl-2-(4-morpholino-butyryl)-hydrazine are mixed with 36 ml. of $POCl_3$ and are heated at 90°C for 25 minutes.

The excess of $POCl_3$ is then evaporated off and the residue is purified by crystallization from methanol. Yield 8 g. (56%). The title product melts at 275 –8° C. The procedure of Example 1 is repeated substituting the indicated hydrazines in place of that of Example 1 and $PCl_5$ as the condensing agent in place of $POCl_3$.

EXAMPLE 2 – 4

| Example No. | End compound: 2-iminoindoline hydrochloride | Starting hydrazine | Condensing agent and its molar ratio to the hydrazine component | | Solvent | Temper. °C | Time hour | Yield % | M.p.°C |
|---|---|---|---|---|---|---|---|---|---|
| 2 | 1-Methyl-3-chloro | 1-phenyl-1-methyl-2-chloroacetyl | PCl$_5$ | 1 | benzene | 50 | 1 | 36 | 217–250(dec.) |
| 3 | 1-Carbethoxymethyl-3,3-dimethyl | 1-phenyl-1-carbethoxymethyl-2-isobutyryl | PCl$_5$ | 1 | benzene | 80 | 0.60 | 35 | 218–219 |
| 4 | 1-Methyl-3-(2-carbomethoxyethyl)- | 1-phenyl-1-methyl-2-(4-carbomethoxybutyryl)- | PCl$_5$ | 1 | benzene | 60 | 0.5 | 85 | 206 (dec.) |

EXAMPLES 5–21

By following the procedure of the previous Examples the following compounds are prepared:
5. 3-Carbomethoxymethyl-2-imino-1-methylindoline hydrochloride. M.p. 251°–3° C (dec.)
6. 2-Amino-3-(p-chlorophenyl)-1-methylindole hydrochloride. M.p. 230°–260° C (dec.)
7. 2-Imino-1-methyl-3-(2-phthalimido-ethyl)indoline hydrochloride. M.p. 258–267° C (dec.)
8. 2-Amino-3-(p-anisyl)-1-methylindole hydrochloride. M.p. 232° C.
9. 2-Amino-3-(m-anisyl)-1-methylindole hydrochloride. M.p. 239°–244° C (dec.)
10. 3-(p-Anisyl)-1-carbethoxymethyl-2-aminoindole hydrochloride. M.p. 215°–216° C (dec.)
11. 3-(2-Dimethylaminoethyl)-2-imino-1-methylindoline dihydrochloride. M.p. 235°–40° C (the compound crystallizes with 0.5 moles of water).
12. 3-(2-Chloroethyl)-2-imino-1-methylindoline hydrochloride. M.p. 223°–226° C.
13. 2'-Imino-1'-methyl-spyro(cyclohexane-1,3'-indoline)hydrochloride. M.p. 351° C.
14. 1-(Carbethoxymethyl-2-imino-3-methyl-3-phenylindoline hydrochloride. M.p. 234°–235° C.
15. 3-(3-Carbomethoxypropyl)-2-imino-1-methylindoline hydrochloride. M.p. 205°–210° C.
16. 1-Benzyl-3-(2-carbomethoxyethyl)-2-iminoindoline hydrochloride. M.p. 226°–228° C (dec.)
17. 3-(3-Chloropropyl)-1-methyl-2-iminoindoline hydrochloride. M.p. 229°–231° C.
18. 2-Imino-1'-methyl-spiro(cyclopentane-1,3'-indoline)hydrochloride. M.p. 325°–330° C.
19. 2-Amino-3-(2-carbomethoxyethyl)-5-methoxy-1-methylindole hydrochloride. M.p. 230°–231° C.
20. 2-Amino-1-methyl-3-(p-nitrophenyl)indole hydrochloride. M.p. 230°–235° C.
21. 1-(2-carbomethoxyethyl)-3,3-dimethyl-2-iminoindoline hydrochloride. M.p. 177°–181° C. C Other derivatives which may be prepared according to the same procedure employed for the above compounds are the following:
2'-Imino-1'-phenyl-spiro(cyclohexane-1,3'-indoline)hydrochloride  2'-Imino-spiro(cyclohexane-1,3'-indoline)hydrochloride  3,3-diethyl-1-methyl-2-iminoindoline hydrochloride.

EXAMPLE 22

2-Acetylamino-3-(p-chlorophenyl)-1-methylindole.

To ten grams of 2-amino-3-(p-chlorophenyl)-1-methylindole hydrochloride in 80 ml. of pyridine, 5.4 ml. acetic anhydride are added under stirring at 20°–25° C. After five hours the pyridine is distilled off in vacuo at 40°–45° C and the oily residue solidifies with water. The product is crystallized from methanol. Yield 7.9 g. M.p. 196°–197° C.

EXAMPLE 23

2-Acetylamino-3-(carbomethoxymethyl)-1-methylindole

The title compound is obtained by reacting 2-amino-3-(carbomethoxymethyl)-1-methylindole hydrochloride with acetic anhydride according to the procedure described in Example 22. M.p. 126°–8° C.

EXAMPLE 24

2-Acetamido-3-(p-acetamidophenyl)-1-methylindole

The title compound is obtained by reacting 2-amino-3-(p-aminophenyl)-1-methylindole hydrochloride with an acetic anhydride excess in the presence of pyridine as the solvent; m.p. 234°–237° C.

EXAMPLE 25

2-(p-Chlorobenzoylimino)-1,3,3-trimethylindoline

By reacting 15 g. of the hydrochloride of 2-imino-1,3,3-trimethylindoline (m.p. 271°–273° C) in 100 ml. of pyridine with 16.30 g. of p-chlorobenzoylchloride at the room temperature for 5 hours, 15.2 g. of the title compound are obtained. B.p. 192° C/0.1 mmHg.

EXAMPLES 26–30

By operating substantially according to Example 25 but employing the properaminoindoles and acid chlorides the following compounds are obtained:
26. 2-Carbethoxyamino-1-methyl-3-phenylindole. M.p. 159°–161° C, from 2-amino-1-methyl-3-phenylindole hydrochloride (m.p. 159°–161° C) and ethyl chlorocarbonate.
27. 2-Benzoylamino-1-methyl-3-phenylindole. M.p. 240°–242° C; from 2-amino-1-methyl-3-phenylindole hydrochloride and benzoyl chloride.
28. 2-Benzoylimino-1,3,3-trimethylindoline. M.p. 102°–103° C; from 2-imino-1,3,3-trimethylindoline hydrochloride and benzoyl chloride.
29. 2-(p-Chlorobenzoylamino)-1-methyl-3-phenylindole. M.p. 245°–6° C; from 2-amino-1-methyl-3-phenylindole hydrochloride and p-chlorobenzoyl chloride.
30. 1-(p-Chlorobenzoyl)-3,3-dimethyl-2-methyliminoindoline. M.p. 102°–104° C; from 3,3-dimethyl-2-methyliminoindoline (m.p. 216°–7° C) and p-chlorobenzoyl chloride.

EXAMPLE 31

2-Acetylamino-3-carboxymethyl-1-methylindole.

To a solution of 3.7 g. of 2-acetamido-3-carbethoxymethyl-1-methylindole in 37 ml. of methanol and 5 ml. of dichloromethane, 15.5 ml. of 1N sodium hydroxide are added at 0° C. The mixture is allowed to stand overnight and then it is neutralized with acetic acid and then evaporated to dryness. The oily residue is taken up with diluted hydrochloric acid and the solid which forms is washed with water. The product is purified by crystallization from ethanol. Yield 3.07 g., m.p. 200°–206° C.

EXAMPLES 32-33

By operating substantially according to the procedure of Example 31 the following compounds are obtained.

32. 1-Carboxymethyl-3,3-dimethyl-2-iminoindoline, m.p. 263°–7° C; from the hydrochloride of the corresponding 1-carbethoxymethyl derivative.

33. 1-Carboxymethyl-3-methyl-3-phenyl-2-iminoindoline, m.p. 219°–222° C; from the hydrochloride of the corresponding 1-carbethoxymthyl derivative.

EXAMPLE 34

3-(p-Chlorophenyl)-1-methyl-2-phenylureidoindole.

To a suspension of 7.8 g. of 2-amino-3-(p-chlorophenyl)-1-methylindole hydrochloride in 150 ml. of ethyl acetate, 60 ml. of 5% sodium hydroxide are added under stirring at room temperature. When the solid has disappeared the organic phase is washed with water and after drying over sodium sulfate, 3.33 ml. of phenylisocyanate are added. The mixture is maintained at 50° C for three hours and then after addition of 2 ml. of phenyliacyanate it is refluxed for three hours. Evaporation of the solvent to a small volume gives 9.5 g. of the title product which after crystallization does not melt up to 300° C.

EXAMPLE 35

3-Phenyl-2-(3-phenylureido)-indole.

The compound is obtained according to Example 34 by reacting 2-amino-3-phenylindole (m.p. 220°–223° C) with phenylisocyanate. M.p. 210°–212° C.

EXAMPLE 36

1-Carbamylmethyl-3,3-dimethyl-2-iminoindoline.

To a solution of 25 ml. of 32% ammonium hydroxide and 15 ml. of ethanol, 4.5 g. of 1-carbethoxymethyl-3,3-dimethyl-2-iminoindoline hydrochloride are added. After 15 hours the reaction mixture is evaporated to dryness and the residue is crystallized from chloroform giving 3,5 g. of the product of the title, melting at 167°–173° C.

EXAMPLE 37

2-Amino-3(p-aminophenyl)-1-methylindole hydrochloride.

The compound is obtained by hydrogenating at room temperature and atmospheric pressure in the presence 10% Pd on charcoal an ethanol solution of the hydrochloride of 2-amino-1-methyl-3-(p-nitrophenyl) indole. Yield 53%, m.p. 258°–261° C.

PREPARATION OF THE 2-ACYL-1-PHENYL HYDRAZINES

A general method for preparing the starting 2-acyl-1-phenyl hydrazine is the following which is described for 1-phenyl-1-methyl-2-cyclohexanoyl hydrazine:

1-Phenyl-1-methylhydrazine (43.3 g.) is dissolved in 1200 ml. of ethyl ether and 53 ml. of triethylamine. To this mixture a solution of 52 g. of cyclohexanoyl chloride in 300 ml. of ethyl ether is added at 0°–5° C. After stirring at the room temperature for one hour the solid precipitate is recovered by filtration and then dissolved in a two phases system chloroform/water. The organic phase is evaporated to dryness and the solid residue is purified by crystallization from ethanol/water. Yield 75 g. M.p. 141°–142° C.

These other following compounds are accordingly prepared:

1-Phenyl-1-methyl-2-(4-morpholino-butyryl)-hydrazine - oily 1-Phenyl-1-carbethoxymethyl-2-(2-phenylpropionyl)-hydrazine. M.p. 93°–94° C.

1-Phenyl-1-benzyl-2-isobutyrylhydrazine. M.p. 126°–128° C.

1,1-Diphenyl-2-isobutyrylhydrazine. M.p. 176°–177° C.

1-Phenyl-1-methyl-2-(2-phenylpropionyl)-hydrazine. M.p. 128°–130° C.

1-Phenyl-1-methyl-2-chloroacetylhydrazine. M.p. 75° C.

1-Phenyl-1-methyl-2-(2-methylbutyryl)-hydrazine. B.p. 190/0.4 mmHg.

1-Phenyl-1-carbethoxymethyl-2-isobutyrylhydrazine. M.p. 91°–93° C.

1-Phenyl-1-methyl-2-(4-carbomethoxybutyryl)-hydrazine. B.p. 193°–196° C/0.6 mmHg.

1-Phenyl-1-methyl-2-(3-carbomethoxypropionyl)-hydrazine. B.p. 170° C/0.2 mmHg.

1-Phenyl-1,2-dimethyl-2-isobutyrylhydrazine. B.p. 100/0.4 mmHg.

1-Phenyl-1-methyl-2-(p-chlorophenylacetyl)-hydrazine. M.p. 149°–152° C.

1-Phenyl-1-methyl-2-(4-phthalimido-butyryl)-hydrazine. M.p. 132°–137° C.

1-Phenyl-1-methyl-2-(p-methoxyphenylacetyl)-hydrazine. M.p. 159°–160° C.

1-Phenyl-1-methyl-2-(m-methoxyphenylacetyl)-hydrazine. M.p. 68°–70° C.

1-Phenyl-1-carbethoxymethyl-2-(p-methoxyphenylacetyl)-hydrazine. M.p. 92°–94° C.

1-Phenyl-1-methyl-(4-dimethylaminobutyryl)-hydrazine hydrochloride. M.p. 165°–167° C.

1-(p-Methoxyphenyl)-1-methyl-2-isobutyrylhydrazine. M.p. 95°–97° C.

1-Phenyl-1-methyl-2-(4-chlorobutyryl)-hydrazine. - oily

1-Phenyl-1-methyl-2-(5-carbomethoxyvaleryl)-hydrazine. B.p. 215/0.4 mmHg.

1-Phenyl-1-benzyl-2-(4-carbomethoxybutyryl)-hydrazine. B.p. 215/0.1 mmHg.

1-Phenyl-2-methyl-2-isobutyrylhydrazine. M.p. 96°–97° C.

1-Phenyl-1-methyl-2-cyclopentanoylhydrazine. M.p. 86°–88° C.

1-Phenyl-1-methyl-2-isobutyrylhydrazine. M.p. 102°–105° C.

1-Phenyl-1-methyl-2acetylhydrazine. M.p. 88°–90° C.

1-Phenyl-1-methyl-2-proprionylhydrazine. M.p. 86°–88° C.

1-Phenyl-1-methyl-2-cyclopropanoylhydrazine. M.p. 100°–102° C.

1-Phenyl-1-benzyl-2-methyl- 2-isobutyrylhydrazine. M.p. 77°–78° C.

1-(p-Methoxyphenyl)-1-methyl-2-(4-carbomethoxybutyryl)-hydrazine. B.p. 195° C/0.1 mmHg.

1-Phenyl-1-methyl-2-(p-nitrobenzoyl)-hydrazine. M.p. 168°–170° C.

1-Phenyl-1-carbethoxyethyl-2-isobutyrylhydrazine. M.p. 71°–73° C.

We claim:

1. The compound 2'-imino-1'-methyl-spiro(cyclohexane-1,3'-indoline)hydrochloride, which is useful as an antiinflammatory.

2. A pharmaceutical composition useful as an antiinflammatory containing as the active ingredient the compound of claim 1 in effective amount in combination with a pharmaceutical adjuvant.

* * * * *

UNITED STATES PATENT AND TRADEMARK OFFICE
CERTIFICATE OF CORRECTION

PATENT NO. : 3,984,563
DATED : October 5, 1976
INVENTOR(S) : Giorgio Winters, Nunzio Di Mola It is certified that error appears in the above–identified patent and that said Letters Patent are hereby corrected as shown below:

Column 4, line 31, "hyrolysis" should read --hydrolysis--.

Column 4, line 42, "anti-inflamatory" should read --anti-inflammatory--.

Column 5, between lines 1-23, compound 5, "1-Phenyl-1-methyl-1-(" should read --1-Phenyl-1-methyl-2-(4- --.

Column 5, line 25, "The compounds" should read --The compounds of--.

Column 5, line 39, "aents," should read --agents--.

Column 7, between lines 1-16, second column of table "End compound: 2-iminoindoline" should read --End compound: -2-iminoindoline--.

Column 7, line 39, "1-(Carbethoxymethyl-2-imino-3-methyl-3-" should read --1-Carbethoxy-methyl-2-imino-3-methyl-3- --.

Column 7, line 54, "C.C" should read --C.--.

Column 7, line 59, "indoline)hydrochloride 2'-Imino-spiro(cyclohexane-" should read --indoline)hydrochloride-- new line --2'Imino-spiro(cyclohexane--.

Column 7, line 60, "1,3'-indoline)hydrochloride

UNITED STATES PATENT AND TRADEMARK OFFICE
CERTIFICATE OF CORRECTION

PATENT NO. : 3,984,563
DATED : October 5, 1976

Page 2 of 2

INVENTOR(S) : Giorgio Winters, Nunzio Di Mola

It is certified that error appears in the above-identified patent and that said Letters Patent are hereby corrected as shown below:

3,3-diethyl-1-methyl-2-" should read --1,3'-indoline)hydrochloride-- new line --3,3-diethyl-1-methyl-2- --.

Column 8, line 49, "properaminoindoles" should read --proper aminoindoles--.

Column 9, line 10, "dryness." should read --dryness under vacuum.--.

Column 9, line 25, "1-carbethoxymthyl" should read --1-carbethoxymethyl--.

Column 9, line 38, "phenyliacyanate" should read --phenylisocyanate--.

Column 10, line 20, "zine - oily 1-Phenyl-1-carbethoxymethyl-2-(2-phenyl-" should read --zine - oily-- new line --1-Phenyl-1-carbethoxymethyl-2-(2-phenyl- --.

Column 10, line 66, "1-Phenyl-1-methyl-2acetylhydrazine." should read --1-Phenyl-1-methyl-2-acetylhydrazine.--.

Signed and Sealed this

Nineteenth Day of April 1977

[SEAL]

Attest:

RUTH C. MASON
Attesting Officer

C. MARSHALL DANN
Commissioner of Patents and Trademarks